(12) United States Patent
White et al.

(10) Patent No.: US 10,112,123 B2
(45) Date of Patent: Oct. 30, 2018

(54) FRACTIONATOR FOR SEPARATING SOLUBILIZED RUBBER FROM A CO-SOLVENT BASED MISCELLA AND RELATED PROCESSES

(71) Applicant: Bridgestone Corporation, Chuo-ku (JP)

(72) Inventors: Robert White, Gilbert, AZ (US); Michael R. Hartzell, Gold Canyon, AZ (US)

(73) Assignee: Bridgestone Corporation, Chuo-ku (JP)

( * ) Notice: Subject to any disclaimer, the term of this patent is extended or adjusted under 35 U.S.C. 154(b) by 0 days.

(21) Appl. No.: 15/512,150

(22) PCT Filed: Sep. 15, 2015

(86) PCT No.: PCT/US2015/050138
§ 371 (c)(1),
(2) Date: Mar. 17, 2017

(87) PCT Pub. No.: WO2016/044240
PCT Pub. Date: Mar. 24, 2016

(65) Prior Publication Data
US 2017/0246555 A1     Aug. 31, 2017

Related U.S. Application Data

(60) Provisional application No. 62/052,944, filed on Sep. 19, 2014.

(51) Int. Cl.
| | | |
|---|---|---|
| *C08G 63/02* | (2006.01) |
| *B01D 11/02* | (2006.01) |
| *C08C 1/04* | (2006.01) |
| *C08C 2/02* | (2006.01) |
| *C07B 63/00* | (2006.01) |
| *C08C 2/06* | (2006.01) |
| *C11D 3/16* | (2006.01) |
| *B01D 17/02* | (2006.01) |

(52) U.S. Cl.
CPC .......... *B01D 11/02* (2013.01); *B01D 17/0214* (2013.01); *C07B 63/00* (2013.01); *C08C 1/04* (2013.01); *C08C 2/02* (2013.01); *C08C 2/06* (2013.01); *C11D 3/16* (2013.01)

(58) Field of Classification Search
USPC ....................................... 528/493
See application file for complete search history.

(56) References Cited

U.S. PATENT DOCUMENTS

| | | | |
|---|---|---|---|
| 4,623,713 A | 11/1986 | Cole et al. |
| 4,681,929 A | 7/1987 | Cole et al. |
| 4,900,445 A | 2/1990 | Flanigan et al. |
| 2006/0149015 A1 | 7/2006 | Cornish et al. |
| 2011/0021743 A1 | 1/2011 | Cornish et al. |
| 2011/0054051 A1 | 3/2011 | Cole et al. |

FOREIGN PATENT DOCUMENTS

| | | | | |
|---|---|---|---|---|
| DE | 2450715 A1 | 4/1976 | | |
| WO | WO-2013134429 A1 * | 9/2013 | ............... | C08C 1/04 |

OTHER PUBLICATIONS

International Preliminary Report on Patentability and Written Opinion from PCT/US2015/050138, dated Mar. 21, 2017 (8 pages).
International Search Report from PCT/US2015/050138, dated Jan. 7, 2016 (4 pages).
European Supplemental Search Report and European Search Opinion from EP application No. 15842390.5, dated May 15, 2018 (7 pages).
Response filed in EP application No. 15842390.5 dated Oct. 2, 2017 with amended claims (8 pages).
Clark, Jim, "Fractional Distillation of Ideal Mixtures of Liquids," copyright 2005 (6 pages), downloaded from http://chemguide.co.uk/physical/phaseeqia/idealfract.html.

* cited by examiner

*Primary Examiner* — Terressa Boykin
(74) *Attorney, Agent, or Firm* — Meredith E. Hooker; Jenny L. Sheaffer

(57) ABSTRACT

Provided herein is a fractionator and related process for separating solubilized rubber from a co-solvent based miscella.

20 Claims, 6 Drawing Sheets

FRACTIONATOR FOR SEPARATING SOLUBILIZED RUBBER FROM A CO-SOLVENT BASED MISCELLA AND RELATED PROCESSES

FIELD

The present disclosure relates to a fractionator and processes that utilize the fractionator. More particularly, the present disclosure relates to a fractionator for separating solubilized rubber from a co-solvent based miscella and related processes.

BACKGROUND

Despite current technologies for producing synthetic rubber, natural rubber from sources such as the *Hevea* plant or tree (also called *Hevea brasiliensis* or a rubber tree) is still considered to possess certain superior properties as compared to synthetic rubber. A number of natural rubber sources such as *Hevea brasiliensis, Ficus elastic* (India rubber tree) and *Cryptostegia grandiflora* (Madagascar rubbervine) produce natural rubber in the form of a sap where the rubber is suspended in an aqueous solution that flows freely and can be recovered by tapping of the plant. Various non-*Hevea* plants are also known to contain natural rubber, but their rubber is stored within the individual cells of the plant (e.g., stems, roots, leaves) and cannot be accessed by tapping but can only be accessed by breaking down the cell walls by physical or other means. When rubber from within the cells of these non-*Hevea* plants is accessed, additional processing is required to separate the rubber from the various other materials. In certain processes for recovering rubber from non-*Hevea* plants, a miscella containing solubilized rubber and solubilized resin is produced, which is then processed to recover the rubber.

SUMMARY

Provided herein is a fractionator for separating solubilized rubber from a co-solvent based miscella. Also provided is a process for separating solubilized rubber from a co-solvent based miscella using the fractionator.

In a first embodiment, a fractionator for separating solubilized rubber from a co-solvent based miscella is provided. The fractionator comprises a primary vessel. The primary vessel comprises a feed inlet for feeding a co-solvent based miscella into the primary vessel. When fed into the primary vessel the co-solvent based miscella separates to form (i) a non-polar solvent viscous rubber phase in a lower portion of the primary vessel and (ii) a polar solvent solubilized resin phase above the non-polar solvent viscous rubber phase. In addition, the primary vessel comprises a side outlet for removing the polar solvent solubilized resin phase from the primary vessel. The primary vessel also comprises a bottom outlet for removing the non-polar solvent viscous rubber phase from the primary vessel. The fractionator of the first embodiment can also be understood as comprising: a primary vessel comprising (a) a feed inlet suitable for feeding a co-solvent based miscella into the primary vessel; (b) a lower portion within the primary vessel (suitable for containing a non-polar solvent viscous rubber phase); (c) an upper portion (suitable for containing a polar solvent solubilized resin phase); (d) a side outlet suitable for removing material from the upper portion of the primary vessel (i.e., suitable for removing the polar solvent solubilized resin phase from the primary vessel); and (e) a bottom outlet suitable for removing material from the lower portion of the primary vessel (i.e., suitable for removing the non-polar solvent viscous rubber phase from the primary vessel).

In a second embodiment, a process for separating solubilized rubber from a co-solvent based miscella is provided. The process comprises providing an initial co-solvent based miscella comprising at least one polar solvent, at least one non-polar solvent, solubilized rubber, and solubilized resin, and using a fractionation system comprising multiple fractionators in series to separate the initial co-solvent based miscella into at least two phases. The multiple fractionators include a first fractionator, one or more intermediate fractionators, and a final fractionator. Each fractionator comprises a primary vessel having a (i) feed inlet, (ii) a side outlet, (iii) a bottom outlet, and (iv) an internal weir between the interior of the primary vessel and the side outlet or an overflow vessel external to the primary vessel and fluidly connected to the side outlet.

According to the processes of the second embodiment, the initial co-solvent based miscella is fed into the first fractionator primary vessel through the first fractionator primary vessel feed inlet, and the initial co-solvent based miscella separates to form (i) a first non-polar viscous rubber phase in a lower portion of the first fractionator primary vessel and (ii) a first polar solvent solubilized resin phase above the first non-polar viscous rubber phase. A first vapor blanket is maintained above the first polar solvent solubilized resin phase in an upper portion of the first fractionator primary vessel. At least a portion of the first polar solvent solubilized resin phase is allowed to flow over the internal weir of the first fractionator or into the overflow vessel of the first fractionator for removal from the first fractionator primary vessel through the side outlet. In addition, the first non-polar solvent viscous rubber phase is allowed to flow out of the bottom outlet of the first fractionator primary vessel and into an intermediate fractionator. Additional polar solvent and optionally additional non-polar solvent is added to the intermediate fractionator primary vessel to form a co-solvent based miscella mixture with the non-polar solvent viscous rubber phase from the first fractionator primary vessel and the mixture is allowed to separate into (i) an intermediate non-polar solvent viscous rubber phase in a lower portion of the intermediate fractionator primary vessel and (ii) an intermediate polar solvent solubilized resin phase above the intermediate non-polar solvent viscous rubber phase. An intermediate vapor blanket is maintained above the intermediate polar solvent solubilized resin phase in an upper portion of the intermediate fractionator primary vessel. At least a portion of the intermediate polar solvent solubilized resin phase is allowed to flow over the internal weir of the intermediate fractionator or into the overflow vessel of the intermediate fractionator for removal from the intermediate fractionator primary vessel through the side outlet. The intermediate non-polar solvent viscous rubber phase is allowed to flow out of the bottom outlet of the intermediate fractionator primary vessel and into the final fractionator. Additional polar solvent and optionally additional non-polar solvent is added to the final fractionator primary vessel to form a co-solvent based miscella mixture with the non-polar solvent viscous rubber phase from the intermediate fractionator primary vessel and the mixture is allowed to separate into (i) a final non-polar solvent viscous rubber phase in a lower portion of the final fractionator primary vessel and (ii) a final polar solvent solubilized resin phase above the final non-polar solvent viscous rubber phase. A final vapor blanket is maintained above the final polar solvent solubilized resin phase in an upper portion of the final fractionator primary vessel. At least a portion of the final polar solvent solubilized resin phase is allowed to flow over the internal weir of the final fractionator or into the overflow vessel of the final fractionator for removal from the final fractionator primary vessel. The final non-polar solvent viscous rubber phase is allowed to flow out of the bottom outlet of the final fractionator primary vessel, thereby providing a separated solubilized rubber phase with reduced resin and polar solvent content as compared to the initial co-solvent based miscella.

DETAILED DESCRIPTION

Figure 1:
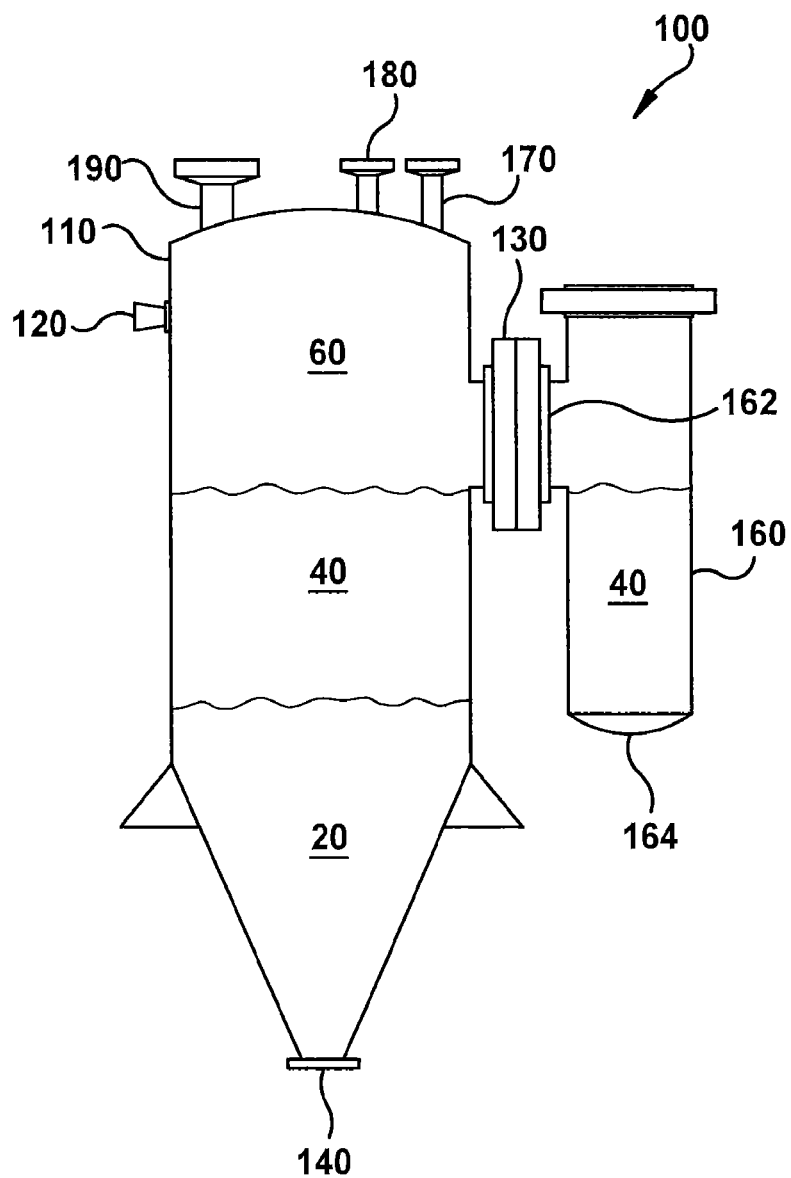
FIG. 1 is a partial cutaway view of an embodiment of a fractionator with an overflow vessel.

Provided herein is a fractionator for separating solubilized rubber from a co-solvent based miscella. Also provided is a process for separating solubilized rubber from a co-solvent based miscella that uses multiple fractionators. For ease of description in certain sections, the fractionator and the process are described as embodiments; the use of this terminology is for ease of description only and should not be interpreted as limiting.

Definitions

The terminology as set forth herein is for description of the embodiments only and should not be construed as limiting the invention as a whole.

As used herein, the term "non-*Hevea* plant" is intended to encompass plants that contain natural rubber within the individual cells of the plant.

As used herein the term "resin" means the naturally occurring non-rubber chemical entities present in a co-solvent based miscella produced from a non-*Hevea* plant, including but not limited to resins (such as terpenes), fatty acids, proteins, and inorganic materials.

Details

In a first embodiment, a fractionator for separating solubilized rubber from a co-solvent based miscella is provided. The fractionator comprises a primary vessel. The primary vessel comprises a feed inlet for feeding a co-solvent based miscella into the primary vessel. When fed into the primary vessel the co-solvent based miscella separates to form two phases, (i) a non-polar solvent viscous rubber phase in a lower portion of the primary vessel and (ii) a polar solvent solubilized resin phase above the non-polar solvent viscous rubber phase. In addition, the primary vessel comprises a side outlet for removing at least a portion of the polar solvent solubilized resin phase from the primary vessel. In certain embodiments, at least a majority of the polar solvent solubilized resin phase, and preferably substantially all of the polar solvent solubilized resin phase (i.e., at least 90% by volume) is removed in this manner. It should be understood that a relatively minor amount of polar solvent and solubilized resin may remain associated with the non-polar solvent viscous rubber phase. The primary vessel also comprises a bottom outlet for removing the non-polar solvent viscous rubber phase from the primary vessel.

In a second embodiment, a process for separating solubilized rubber from a co-solvent based miscella is provided. The process comprises providing an initial co-solvent based miscella comprising at least one polar solvent, at least one non-polar solvent, solubilized rubber, and solubilized resin, and using a fractionation system comprising multiple fractionators in series to separate the initial co-solvent based miscella into at least two phases. The multiple fractionators include a first fractionator, one or more intermediate fractionators, and a final fractionator. Each fractionator comprises a primary vessel having (i) a feed inlet, (ii) a side outlet, (iii) a bottom outlet, and (iv) an internal weir between the interior of the primary vessel and the side outlet or an overflow vessel external to the primary vessel and fluidly connected to the side outlet.

According to the process of the second embodiment, the initial co-solvent based miscella is fed into the first fractionator primary vessel through the first fractionator primary vessel feed inlet, and the initial co-solvent based miscella separates to form (i) a first non-polar viscous rubber phase in a lower portion of the first fractionator primary vessel and (ii) a first polar solvent solubilized resin phase above the first non-polar viscous rubber phase. A first vapor blanket is maintained above the first polar solvent solubilized resin phase in an upper portion of the first fractionator primary vessel. At least a portion of the first polar solvent solubilized resin phase is allowed to flow over the internal weir of the first fractionator or into the overflow vessel of the first fractionator for removal from the first fractionator primary vessel through the side outlet. In certain embodiments, at least a majority of the polar solvent solubilized resin phase, and preferably substantially all of the polar solvent solubilized resin phase (i.e., at least 90% by volume) is removed in this manner. It should be understood that a relatively minor amount of polar solvent and solubilized resin may remain associated with the non-polar solvent viscous rubber phase. In addition, the first non-polar solvent viscous rubber phase is allowed to flow out of the bottom outlet of the first fractionator primary vessel and into an intermediate fractionator. Additional polar solvent and optionally additional non-polar solvent (any of which may be the same or different than the at least one polar solvent and the at least one non-polar organic solvent contained in the initial co-solvent based miscella) is added to the intermediate fractionator primary vessel to form a co-solvent based miscella mixture with the non-polar solvent viscous rubber phase from the first fractionator primary vessel and the mixture is allowed to separate into (i) an intermediate non-polar solvent viscous rubber phase in a lower portion of the intermediate fractionator primary vessel and (ii) an intermediate polar solvent solubilized resin phase above the intermediate non-polar solvent viscous rubber phase. An intermediate vapor blanket is maintained above the intermediate polar solvent solubilized resin phase in an upper portion of the intermediate fractionator primary vessel. At least a portion of the intermediate polar solvent solubilized resin phase is allowed to flow over the internal weir of the intermediate fractionator or into the overflow vessel of the intermediate fractionator for removal from the intermediate fractionator primary vessel through the side outlet. The intermediate non-polar solvent viscous rubber phase is allowed to flow out of the bottom outlet of the intermediate fractionator primary vessel and into the final fractionator. Additional polar solvent and optionally additional non-polar solvent (any of which may be the same or different than the at least one polar solvent and the at least one non-polar organic solvent contained in the initial co-solvent based miscella) is added to the final fractionator primary vessel to form a co-solvent based miscella mixture with the non-polar solvent viscous rubber phase from the intermediate fractionator primary vessel and the mixture is allowed to separate into (i) a final non-polar solvent viscous rubber phase in a lower portion of the final fractionator primary vessel and (ii) a final polar solvent solubilized resin phase above the final non-polar solvent viscous rubber phase. A final vapor blanket is maintained above the final polar solvent solubilized resin phase in an upper portion of the final fractionator primary vessel. In certain embodiments, the vapor blanket comprises air or nitrogen gas. At least a portion of the final polar solvent solubilized resin phase is allowed to flow over the internal weir of the final fractionator or into the overflow vessel of the final fractionator for removal from the final fractionator primary vessel. The final non-polar solvent viscous rubber phase is allowed to flow out of the bottom outlet of the final fractionator primary vessel, thereby providing a separated solubilized rubber phase with reduced resin and polar solvent content as compared to the initial co-solvent based miscella.

The Fractionator

Referring now to FIG. 1, a partial cutaway view of a fractionator (100) according to the first embodiment is shown. The fractionator (100) is useful for separating solubilized rubber from a co-solvent based miscella. As seen in FIG. 1, the fractionator (100) comprises a primary vessel (110). In certain embodiments, the primary vessel (110) has a cone-shaped lower portion. The primary vessel (110) comprises a feed inlet (120) for feeding a co-solvent based miscella into the primary vessel (110). When fed into the primary vessel (110) the co-solvent based miscella separates to form (i) a non-polar solvent viscous rubber phase (20) in a lower portion of the primary vessel (110) and (ii) a polar solvent solubilized resin phase (40) above the non-polar solvent viscous rubber phase. The line of separation between the non-polar solvent viscous rubber phase (20) and the polar solvent solubilized resin phase (40) is also referred to herein as the phase interface level. It should be understood that the phase interface level may vary in height during operation of the fractionator. As well, the relative volume of the polar solvent solubilized resin phase and the non-polar solvent viscous rubber phase during operation, may vary depending upon the respective polar and non-polar solvents utilized, the size of the fractionator and the desired residence time within the fractionator. In addition, the primary vessel (110) comprises a side outlet (130) for removing the polar solvent solubilized resin phase (40) from the primary vessel (110). The primary vessel (110) also comprises a bottom outlet (140) for removing the non-polar solvent viscous rubber phase (20) from the primary vessel (110).

Figure 2:
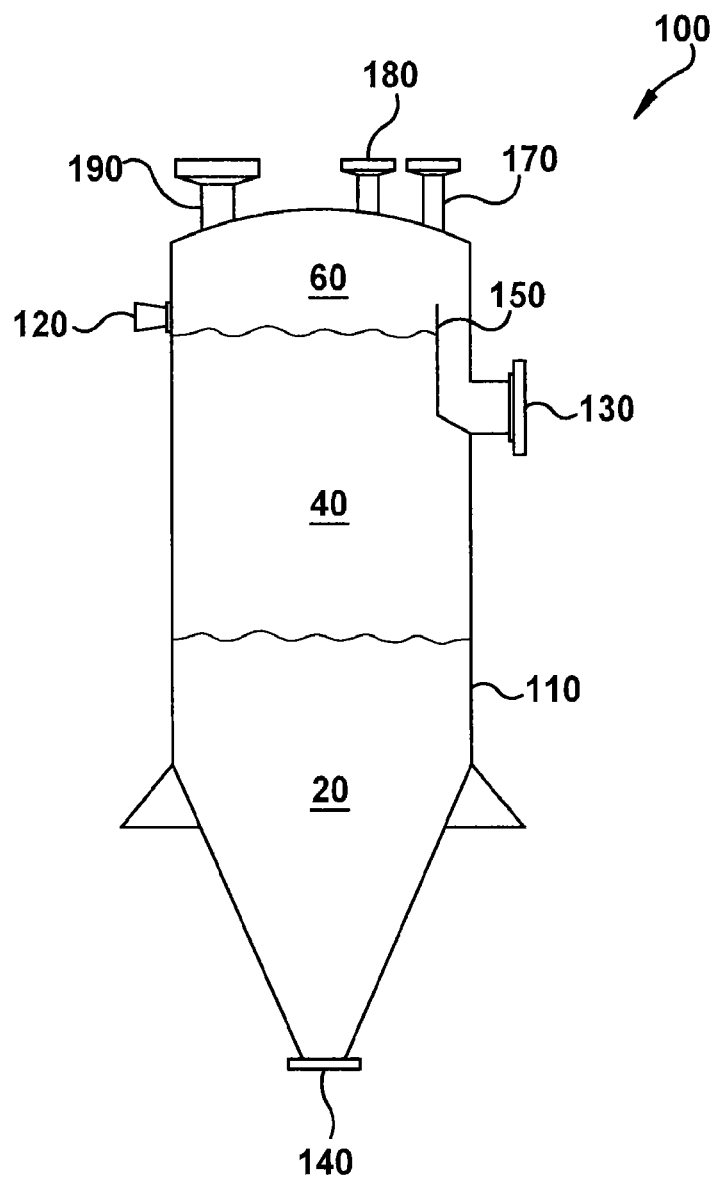
FIG. 2 is a partial cutaway view of an embodiment of a fractionator with an internal weir.
Figure 3:
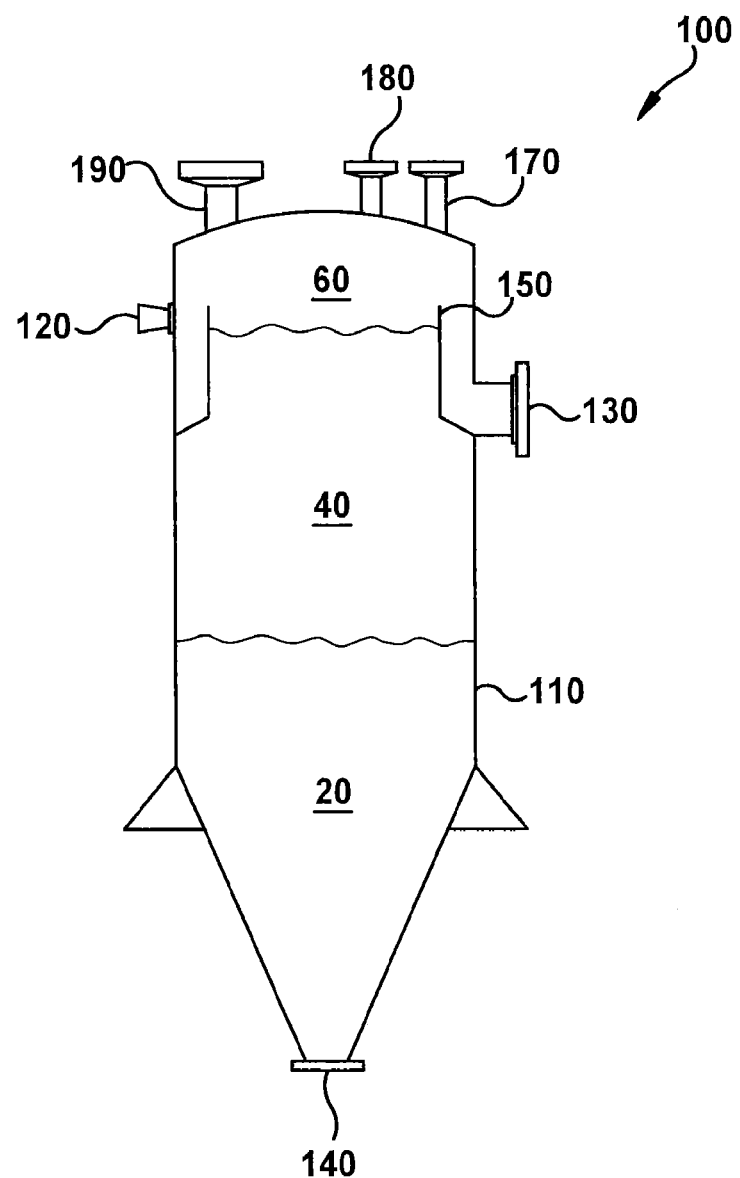
FIG. 3 is a partial cutaway view of an embodiment of a fractionator with an internal weir.

In certain embodiments, the primary vessel (100) of the fractionator (100) comprises additional inlets and outlets for feeding and removing additional components. For example, the primary vessel (110) may comprise a gas inlet (170) and a gas outlet, as seen in FIGS. 1-3. The gas inlet (170) may be used to add a vapor blanket (60) to the fractionator (100), for example, above the polar solvent solubilized resin phase (40). Similarly, the gas outlet (180) may be used to purge or vent vapor from the fractionator (100). The optional gas inlet may also be understood as suitable for adding a vapor blanket to the fractionator (e.g., within the upper portion of the primary vessel). The optional gas outlet may also be understood as suitable for purging or venting vapor from the fractionator (e.g., from within the upper portion of the primary vessel).

With continued reference to FIGS. 1-3, in certain embodiments, the primary vessel (110) comprises at least one solvent inlet (190) for feeding additional solvent to the primary vessel (110). It should be understood that the at least one solvent inlet (190) may be a polar solvent inlet for adding polar solvent to the fractionator (100) or a non-polar solvent inlet for adding non-polar solvent to the fractionator (100). In certain embodiments, the primary vessel (110) comprises a polar solvent inlet for adding polar solvent to the fractionator (100) and a non-polar solvent inlet for adding non-polar solvent to the fractionator (100).

With reference now to FIG. 1, in certain embodiments, the fractionator (100) comprises an overflow vessel (160). The overflow vessel (160) has an inlet (162) and an outlet (164). The overflow vessel inlet (162) is fluidly connected to the side outlet (130) such that at least a portion of the polar solvent solubilized resin phase (40) flows through the side outlet (130) into the overflow vessel (160). The overflow vessel inlet (162) can also be understood as fluidly connected to the side outlet (130) such that at least a portion of material located within the upper portion of the primary vessel may flow through the side outlet (130) into the overflow vessel (160). Accordingly, the overflow vessel (160) assists in controlling the phase interface level in the primary vessel (110) as well as in removing the polar solvent resin phase. The polar solvent solubilized resin phase (40) that is collected in the overflow vessel (160) is removed through the overflow vessel outlet (164). In certain embodiments, at least a majority of the polar solvent solubilized resin phase, and preferably substantially all of the polar solvent solubilized resin phase (i.e., at least 90% by volume) is removed in this manner. It should be understood that a relatively minor amount of polar solvent and solubilized resin may remain associated with the non-polar solvent viscous rubber phase. The side outlet (130) and overflow vessel (160) combination improve the safety of the fractionator (100) by allowing the fractionator (100) to operate without a liquid full volume and also provide better control of the phase interface level.

Referring now to FIGS. 2 and 3, in certain embodiments, the primary vessel (110) comprises an internal weir (150). As seen in FIGS. 2 and 3, the side outlet (130) is bounded by the internal weir (150) such that the polar solvent solubilized resin phase (40) must flow over the internal weir (150) to remove the polar solvent solubilized resin phase (40) through the side outlet (130). In other words, the internal weir (150) provides an interior barrier to the side outlet (130) that must be overcome before the polar solvent solubilized resin phase (40) can be removed from the primary vessel (110) through the side outlet (130). Thus, it can be appreciated that the internal weir (150) assists in controlling the phase interface level in the primary vessel (110). The side outlet (130) and internal weir (150) combination improve the operation of the fractionator (100) by allowing the fractionator (100) to operate without a liquid full volume and by providing better control of the phase interface level.

As seen in FIG. 2, in certain embodiments, the internal weir (150) forms a wall around a portion of the circumference of an upper interior portion of the primary vessel (110). Alternatively, in certain embodiments, the internal weir (150) forms a wall around the entire circumference of an upper interior portion of the primary vessel (110), as shown in FIG. 3. In such embodiments, the feed inlet that feeds the co-solvent based miscella (or the non-polar solvent viscous rubber phase) is positioned so that it feeds material into the interior of the primary vessel and not into the internal weir. As previously mentioned, the internal weir (150) functions to separate the side outlet (130) from the interior volume of the primary vessel (110) occupied by liquid (i.e., the separated co-solvent based miscella) until the level of the polar solvent solubilized resin phase (40) overcomes the internal weir (150) to allow at least a portion of the polar solvent solubilized resin phase (40) to flow from the primary vessel (110) through the side outlet (130). In certain embodiments, at least a majority of the polar solvent solubilized resin phase, and preferably substantially all of the polar solvent solubilized resin phase (i.e., at least 90% by volume) is removed in this manner. It should be understood that a relatively minor amount of polar solvent and solubilized resin may remain associated with the non-polar solvent viscous rubber phase.

Figure 4:
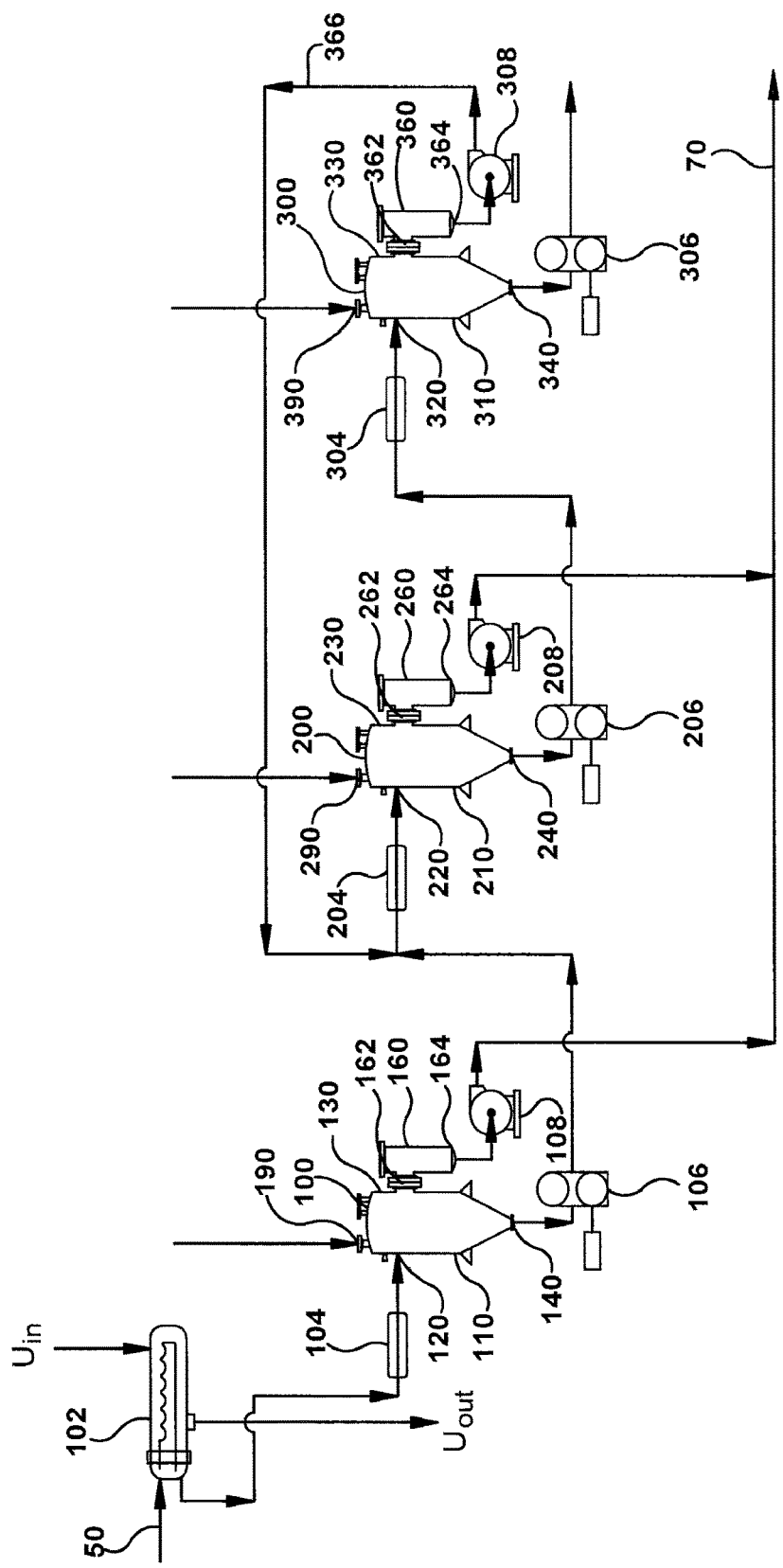
FIG. 4 is a schematic diagram of an embodiment of multiple fractionators connected in series.

In certain embodiments, the fractionator (100) further comprises at least one additional fractionator connected in series, wherein each additional fractionator has a feed inlet that is fluidly connected to the bottom outlet of the preceding fractionator. For example, as seen in FIG. 4, a first fractionator (100) is connected in series with a second fractionator (200) and a third fractionator (300). Although FIG. 4 depicts three fractionators, it should be understood that additional fractionators may be utilized. An initial co-solvent based miscella (50) is fed into the primary vessel (110) of the first fractionator (100) through the feed inlet (120). In certain embodiments, the initial co-solvent based miscella (50) is fed through a heat exchanger (102) (heated or cooled with appropriate plant utilities (U) (e.g., hot water, cooling water)) and/or a static mixer (104) prior to being fed into the primary vessel (110) of the first fractionator (100). As seen in FIG. 4, the bottom outlet (140) of the first fractionator (100) is fluidly connected to the feed inlet (220) of the second fractionator. In certain embodiments, a bottoms pump (106) is fluidly connected to the bottom outlet (140) of the first fractionator (100) and the feed inlet (220) of the second fractionator (200) and operates to transport the non-polar solvent viscous rubber phase from the first fractionator (100) to the second fractionator (200). Similarly, the bottom outlet (240) of the second fractionator (200) is fluidly connected to the feed inlet (320) of the third fractionator (300). As seen in FIG. 4, in certain embodiments, a bottoms pump (206) is fluidly connected to the bottom outlet (240) of the second fractionator (200) and the feed inlet (320) of the third fractionator (300) and operates to transport the non-polar solvent viscous rubber phase from the second fractionator (200) to the third fractionator (300).

With continued reference to FIG. 4, in certain embodiments, each fractionator (100, 200, 300) comprises a polar solvent inlet (190, 290, 390) for adding polar solvent to the fractionator (100, 200, 300). The solubilized rubber is preferentially soluble in the non-polar solvent, and thus, as additional polar solvent is added the relative amount of polar solvent as compared to non-polar solvent is increased so as to cause the solubilized rubber to coagulate to form the non-polar solvent viscous rubber phase. Accordingly, adding additional polar solvent promotes the separation of the solubilized rubber from the solubilized resin. In certain embodiments, polar solvent may be added to a fractionator (100, 200, 300) by providing a polar solvent feed line that is fluidly connected to the feed inlet (120, 220, 320) of the fractionator (100, 200, 300). By way of example, polar solvent may be fed into the third fractionator (300) by providing a polar solvent feed line that connects into the flow stream that enters into the feed inlet (320) of the third fractionator (300).

In certain embodiments, at least one of the fractionators comprises a resin phase feed line that is fluidly connected to the preceding fractionator. For example, as seen in FIG. 4, the third fractionator (300) has a resin phase feed line (366) that is fluidly connected to the second fractionator (200), thus allowing the polar solvent solubilized resin phase of the third fractionator (300) to flow to the second fractionator (200). In certain embodiments, as seen in FIG. 4, a resin pump (308) is fluidly connected to the third fractionator (300) and the feed inlet of the (220) second fractionator and operates to transport the polar solvent solubilized resin phase from the third fractionator (300) to the second fractionator (200).

In certain embodiments, a resin pump (108) is fluidly connected to the first fractionator (100) and a resin tank and operates to transport the polar solvent solubilized resin phase from the first fractionator (100) to the resin tank via stream (70), as seen in FIG. 4. Similarly, in certain embodiments, a resin pump (208) is fluidly connected to the second fractionator (200) and a resin tank and operates to transport the polar solvent solubilized resin phase from the second fractionator (200) to the resin tank via stream (70).

Figure 5:
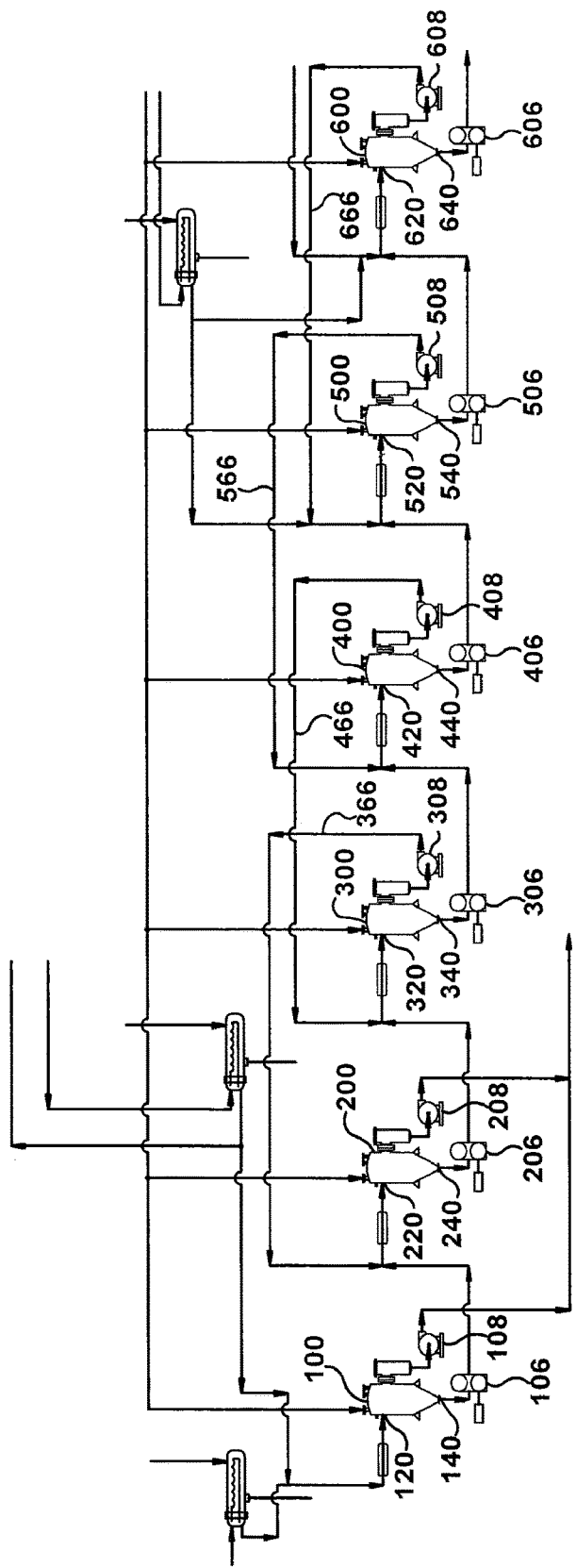
FIG. 5 is a schematic diagram of an embodiment of multiple fractionators connected in series.

In certain embodiments, the fractionator comprises at total of six fractionators connected in series. For example, as seen in FIG. 5, six fractionators (100, 200, 300, 400, 500, 600) are connected in series, wherein each fractionator after the first fractionator (100) has a feed inlet (220, 320, 420, 520, 620) that is fluidly connected to the bottom outlet (140, 240, 340, 440, 540) of the preceding fractionator. For instance, the bottom outlet (140) of the first fractionator (100) is fluidly connected to the feed inlet (220) of the second fractionator (200), the bottom outlet (240) of the second fractionator (200) is fluidly connected to the feed inlet (320) of the third fractionator (300), and so forth. As illustrated in FIG. 5, in certain embodiments, a bottoms pump (106, 206, 306, 406, 506) is fluidly connected to the bottom outlet (140, 240, 340, 440, 540) of a fractionator (100, 200, 300, 400, 500) and the feed inlet (220, 320, 420, 520, 620) of the next successive fractionator (200, 300, 400, 500, 600) and operates to transport the non-polar solvent viscous rubber phase from one fractionator (100, 200, 300, 400, 500) to the next successive fractionator (200, 300, 400, 500, 600).

With continued reference to FIG. 5, in certain embodiments, the fractionator comprises at total of six fractionators connected in series, and at least one of the intermediate fractionators further comprises a resin phase feed line that is fluidly connected to the preceding fractionator. For example, as seen in FIG. 5, the third fractionator (300) comprises a resin phase feed line (366) that is fluidly connected to the second fractionator (200), the fourth fractionator (400) comprises a resin phase feed line (466) that is fluidly connected to the third fractionator (300), and the fifth fractionator (500) comprises a resin phase feed line (566) that is fluidly connected to the fourth fractionator (400). In certain embodiments, the sixth or final fractionator (600) comprises a resin phase feed line (666) that is fluidly connected to the fifth fractionator (500), as illustrated in FIG. 5. In certain embodiments, a resin pump (308, 408, 508, 608) is fluidly connected to the fractionator (300, 400, 500, 600) and the feed inlet of the (220, 320, 420, 520) preceding fractionator and operates to transport the polar solvent solubilized resin phase from one fractionator (300, 400, 500, 600) to the preceding fractionator (200, 300, 400, 500, 600).

The Process

In accordance with the second embodiment, a process for separating solubilized rubber from a co-solvent based miscella is provided. Generally, the process may be characterized as a counter-current solvent extraction process in which solubilized rubber is separated and recovered from an initial co-solvent based miscella. In certain embodiments, the initial co-solvent based miscella comprises about 1 to about 10 weight % rubber (solubilized), about 1 to about 15 weight % resin (solubilized), and about 75 to about 98 weight % combined non-polar and polar solvents. In certain embodiments, the initial co-solvent based miscella comprises about 1 to about 6 weight % rubber (solubilized), about 2 to about 8 weight % resin (solubilized), and about 86 to about 97 weight % combined non-polar and polar solvents. During the process, the resin that is contained within the co-solvent based miscella is separated from the rubber that is also contained therein, relying upon the relatively higher solubility of the rubber in the non-polar solvent and the relatively higher solubility of the resin in the polar solvent. Accordingly, the separated solubilized rubber phase that results from the process comprises relatively less resin and polar solvent than the initial co-solvent based miscella. In certain embodiments, the separated solubilized rubber phase that results comprises 0-6 weight % resin, including about 0.5 to about 4 weight % resin (based on the total dry weight of combined resin and rubber in the separated solubilized rubber phase, i.e., with all solvent removed). In certain embodiments, the separated solubilized rubber phase that results comprises no more than about 6 weight %, no more than about 5 weight %, no more than about 4 weight %, no more than about 3 weight %, no more than about 2 weight %, or no more than about 1 weight % resin (based on the total dry weight of combined resin and rubber in the separated solubilized rubber phase, i.e., with all solvent removed).

Co-Solvent Based Miscella

According to the process of the second embodiment disclosed herein, an initial co-solvent based miscella is provided for processing. The initial co-solvent miscella comprises at least one polar solvent, at least one non-polar solvent, solubilized rubber, and solubilized resin. In certain embodiments, the initial co-solvent based miscella that is processed in accordance with the second embodiment is produced utilizing a non-*Hevea* plant. Exemplary non-*Hevea* plants from which the initial co-solvent based miscella may be produced include, but are not limited to: *Parthenium argentatum* (Guayule shrub), *Taraxacum Kok-Saghyz* (Russian dandelion), *Euphorbia lathyris* (gopher plant), *Parthenium incanum* (mariola), *Chrysothamnus nauseosus* (rabbitbrush), *Pedilanthus macrocarpus* (candililla), *Asclepias syriaca, speciosa, subulata*, et al (milkweeds), *Solidago altissima, graminifolia rigida*, et al (goldenrods), *Cacalia atripilicifolia* (pale Indian plantain), *Pycnanthemum incanum* (mountain mint), *Teucreum canadense* (American germander) and *Campanula Americana* (tall bellflower). Other plants which produce rubber and rubber-like hydrocarbons are known, particularly among the Compositae, Euphorbiaceae, Campanulaceae, Labiatae, and Moracea families. It is contemplated that the initial co-solvent based miscella processed in accordance with the processes disclosed herein may be produced from a single type of non-*Hevea* plant or a mixture of more than one type of non-*Hevea* plant. Accordingly, in certain embodiments, the solubilized rubber of the initial co-solvent based miscella comprises non-*Hevea* rubber. In a preferred embodiment, the non-*Hevea* rubber is from guayule.

In certain embodiments, the initial co-solvent based miscella is held in a storage tank and is provided to the process by conventional means, for example, a pump.

Fractionation System

Figure 6:
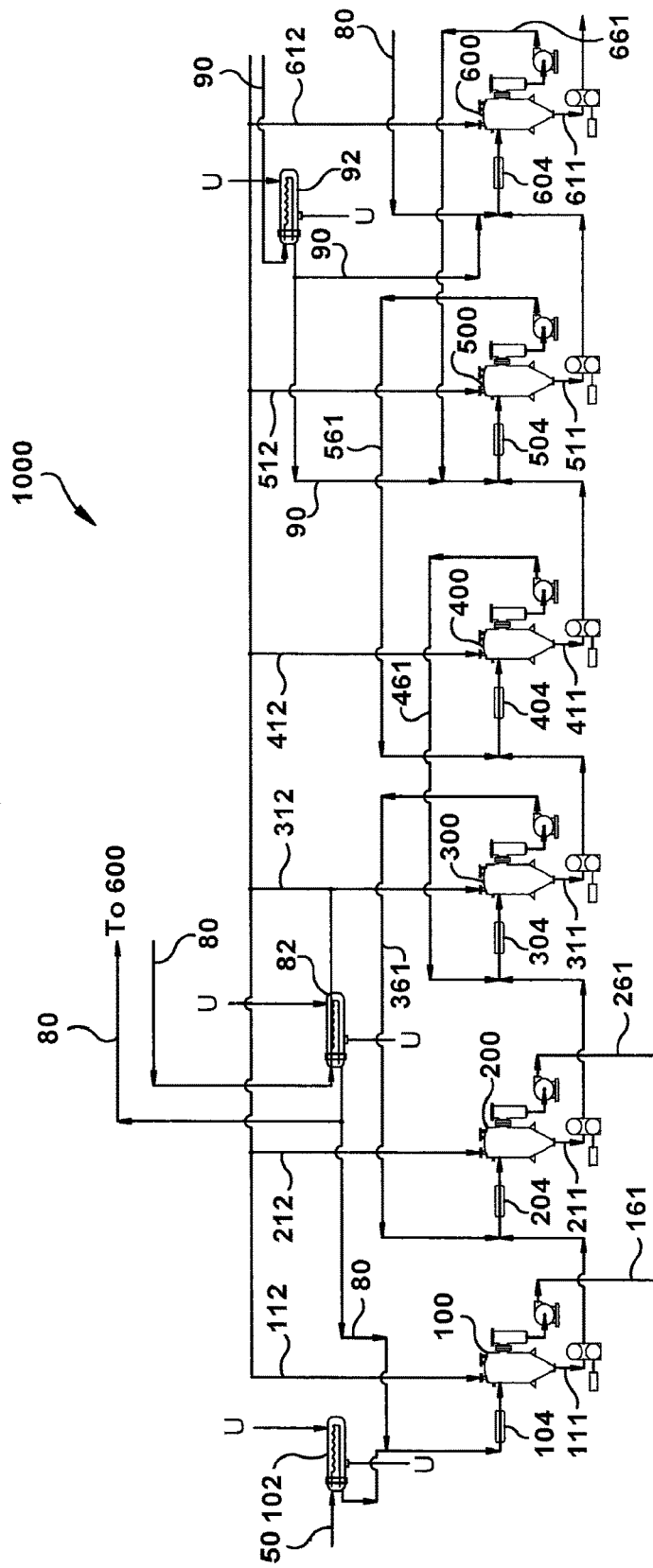
FIG. 6 is a schematic diagram of an embodiment of a process for separating solubilized rubber from a co-solvent based miscella.

The process of the second embodiment disclosed herein use a fractionation system (1000) comprising multiple fractionators in series to separate the initial co-solvent based miscella into at least two phases. As seen in FIG. 6, the multiple fractionators include a first fractionator (100), one or more intermediate fractionators (200, 300, 400, 500), and a final fractionator (600). Although FIG. 6 shows the fractionation system (1000) as having six fractionators, it should be understood that the fractionation system (1000) may have less than six fractionators or more than six fractionators.

The individual fractionators comprising the fractionation system (1000) used in the processes disclosed herein may be configured in accordance with any of the previously described fractionators of the first embodiment, for example, the fractionators shown in FIGS. 1-5. In general, each fractionator comprising the fractionation system (1000) comprises a primary vessel having a feed inlet, a side outlet, and a bottom outlet.

In certain embodiments of the second embodiment, one or more fractionators comprising the fractionation system (1000) comprise an internal weir (150) between the interior of the primary vessel (110) and the side outlet (130), as seen in the fractionators (100) of FIGS. 2 and 3. For example, as shown in FIGS. 2 and 3, in certain embodiments of the second embodiment, the primary vessel of the fractionator (100) comprises an internal weir (150) and the side outlet (130) of the fractionator (100) is bounded by the internal weir (150) such that at least a portion of the polar solvent resin phase (40) flows over the internal weir (150) to remove the polar solvent resin phase (40) through the side outlet (130). In certain embodiments, at least a majority of the polar solvent solubilized resin phase, and preferably substantially all of the polar solvent solubilized resin phase (i.e., at least 90% by volume) is removed in this manner. It should be understood that a relatively minor amount of polar solvent and solubilized resin may remain associated with the non-polar solvent viscous rubber phase. Additionally, the internal weir (150) forms a wall around at least a portion of the circumference of an upper interior portion of the primary vessel (110).

In certain embodiments of the second embodiment, one or more fractionators comprising the fractionation system (1000) comprise an overflow vessel (160) external to the primary vessel (110) and fluidly connected to the side outlet (130), as seen in the fractionator (100) of FIG. 1. For example, as shown in FIG. 1, in certain embodiments of the second embodiment, the fractionator (100) comprises an overflow vessel (160) external to the primary vessel (110). The overflow vessel (160) has an inlet (162) and an outlet (164). The overflow vessel inlet (162) is fluidly connected to the side outlet (130) such that the polar solvent solubilized resin phase (40) flows through the side outlet (130) into the overflow vessel (160). The polar solvent solubilized resin phase (40) that is collected in the overflow vessel (160) is removed through the overflow vessel outlet (164). In certain embodiments, at least a majority of the polar solvent solubilized resin phase, and preferably substantially all of the polar solvent solubilized resin phase (i.e., at least 90% by volume) is removed in this manner. It should be understood that a relatively minor amount of polar solvent and solubilized resin may remain associated with the non-polar solvent viscous rubber phase.

As mentioned above, the multiple fractionators of the fractionation system (1000) are connected in series. In other words, the feed inlet of a fractionator is fluidly connected to a bottom outlet of the preceding fractionator. Accordingly, rubber-containing material (i.e., the non-polar solvent viscous rubber phase) is allowed to flow out of the bottom outlet of a fractionator and into the feed inlet of the next successive fractionator. In certain embodiments of the second embodiment, at least two intermediate fractionators are used and each additional intermediate fractionator is connected in series and positioned between the first fractionator and the final fractionator. For example, in certain embodiments, at least four intermediate fractionators (200, 300, 400, 500) are used, and each intermediate fractionator is connected in series and positioned between the first fractionator (100) and the final fractionator (600), as seen in FIG. 6. It can also be seen that the first fractionator (100) and the final fractionator (600) are connected in series with the intermediate fractionators (200, 300, 400, 500).

Process Flow

With reference now to FIG. 6, the process flow of an embodiment of a process according to the second embodiment will be described. As seen in FIG. 6, the initial co-solvent based miscella (50) is fed into a first fractionator (100). More specifically, the initial co-solvent based miscella is fed into the first fractionator primary vessel through the first fractionator primary vessel feed inlet. In certain embodiments of the processes disclosed herein, the initial co-solvent based miscella (50) flows through a heat exchanger (102) (supplied with appropriate plant utilities (U), e.g., hot water, cooling water, steam, etc.) to control the temperature of the initial co-solvent based miscella (50) entering the first fractionator (100). In certain embodiments of the second embodiment, the temperature of the initial co-solvent based miscella (50) entering the first fractionator (100) is about 50° F. to about 120° F. (about 10° C. to about 50° C.), and preferably about 60 to about 80° F. (about 16° C. to about 27° C.). This particular temperature range of the initial co-solvent based miscella (50) promotes better downstream phase separation in the fractionators.

In certain embodiments of the second embodiment, polar solvent (80) is added to the initial co-solvent based miscella (50) prior to or after the initial co-solvent based miscella (50) is fed into the first fractionator primary vessel. For example, in certain embodiments, the polar solvent (80) is combined with the initial co-solvent based miscella (50) prior to entering the first fractionator (100), as seen in FIG. 6. In other embodiments, the polar solvent (80) is fed directly into the first fractionator (100), such as through a solvent inlet as previously mentioned. In certain embodiments, the polar solvent (80) flows through a heat exchanger (82) to control the temperature of the polar solvent (80) being added to the initial co-solvent based miscella (50). In certain embodiments, the polar solvent (80) is stored in a tank and is provided to the process by conventional means, for example, a pump.

In certain embodiments, where the polar solvent (80) is combined with the initial co-solvent based miscella (50), the combined stream flows through a static mixer (104), as seen in FIG. 6. The static mixer (104) permits gentle mixing of the combined stream of the polar solvent (80) and the initial co-solvent based miscella (50). Accordingly, the static mixer (104) avoids aggressive mixing of the combined stream of the polar solvent (80) and the initial co-solvent based miscella (50), which can lead to problems in achieving the desired phase separation in the fractionators.

After the initial co-solvent based miscella (50) is fed into the first fractionator (100), the initial co-solvent based miscella (50) separates to form (i) a first non-polar solvent viscous rubber phase in a lower portion of the first fractionator primary vessel and (ii) a first polar solvent solubilized resin phase above the first non-polar solvent viscous rubber phase. In certain embodiments, adding additional polar solvent (80) to the initial co-solvent based miscella (50) promotes the separation of the non-polar solvent viscous rubber phase from the polar solvent solubilized resin phase by causing high molecular weight solubilized rubber (preferably rubber with a molecular weight of at least 800,000 (e.g., 800,000-1,500,000), even more preferably at least 1,000,000 (e.g., 1,000,000-1,500,000)) to coagulate, thereby forming the non-polar solvent viscous rubber phase. Lower molecular weight solubilized rubber may remain in the polar solvent solubilized resin phase. The molecular weights of rubber that are referred to herein are determined by GPC, utilizing a polystyrene standard.

As previously mentioned with respect to fractionator of the first embodiment, the fractionators utilized in the fractionation system (1000) of the second embodiment are operated such that a vapor blanket is maintained above the polar solvent solubilized resin phase in an upper portion of the fractionator primary vessel. In certain embodiments, the vapor blanket comprises air or nitrogen gas. Accordingly, the fractionators are operated such that less than the total volume of the fractionator primary vessel is occupied by liquid. As previously mentioned with respect to the fractionator of the first embodiment, in certain embodiments of the second embodiment, the fractionators utilized in the fractionation system (1000) may include a gas inlet and a gas outlet. As seen in FIG. 6, in certain embodiments of the second embodiment, the fractionators may be purged or vented via vent lines (112, 212, 312, 412, 512, 612) to a common vent line header for additional processing.

In certain embodiments of the processes disclosed herein, it may be helpful to allow for some amount of residence time to allow the non-polar solvent viscous rubber phase to separate from the polar solvent solubilized resin phase in the fractionators. The particular residence time will depend upon various factors including, but not limited to, the volume of the fractionator, the flow rate, the particular polar and non-polar solvents utilized, and the rubber content of the miscella. In certain embodiments, the total residence time (i.e., combined time) within all of the fractionators used in the process is about 30 minutes to about 4 hours. With respect to the first fractionator (100), during operation at least a portion of the first polar solvent solubilized resin phase is removed from the first fractionator primary vessel. For example, in certain embodiments of the second embodiment, the first fractionator may comprise an internal weir or an overflow vessel, as previously described, for allowing removal of at least a portion of the first polar solvent solubilized resin phase. In certain embodiments of the second embodiment, the portion of the first polar solvent solubilized resin phase (161) that is removed from the first fractionator (100) is transferred to a resin tank for storage or further processing and is not conveyed to any other fractionator.

With continued reference to FIG. 6, the first non-polar solvent viscous rubber phase (111) is allowed to flow out of the bottom outlet of the first fractionator primary vessel and into an intermediate fractionator (200). Additional polar solvent, and optionally additional non-polar solvent, is added to the intermediate fractionator primary vessel to form a co-solvent based miscella mixture with the non-polar solvent viscous rubber phase from the first fractionator. In certain embodiments of the second embodiment, the additional polar solvent, and optionally additional non-polar solvent, is added directly to the intermediate fractionator (200). In certain embodiments of the second embodiment, the additional polar solvent, and optionally additional non-polar solvent, is combined with the non-polar solvent viscous rubber phase (111) and the combined stream is fed into the intermediate fractionator (200). In certain embodiments of the second embodiment, the additional polar solvent is provided by the polar solvent solubilized resin phase of the next successive fractionator. For example, as seen in FIG. 6, the polar solvent solubilized resin phase (361) removed from intermediate fractionator (300) is combined with the first non-polar solvent viscous rubber phase (111) and the combined stream is fed into intermediate fractionator (200). In certain embodiments, where the polar solvent solubilized resin phase (361) from intermediate fractionator (300) is combined with the first non-polar solvent viscous rubber phase (111), the combined stream flows through a static mixer (204) prior to entering intermediate fractionator (200), as seen in FIG. 6.

After the co-solvent based miscella mixture is fed into the intermediate fractionator (200), the mixture is allowed to separate into (i) an intermediate non-polar solvent viscous rubber phase in a lower portion of the intermediate fractionator primary vessel and (ii) an intermediate polar solvent solubilized resin phase above the intermediate non-polar solvent viscous rubber phase. As previously discussed, during operation of the intermediate fractionator an intermediate vapor blanket is maintained above the intermediate polar solvent solubilized resin phase in an upper portion of the intermediate fractionator primary vessel.

During operation of the intermediate fractionator (200) at least a portion of the intermediate polar solvent solubilized resin phase is removed from the intermediate fractionator primary vessel. For example, in certain embodiments of the second embodiment, the intermediate fractionator may comprise an internal weir or an overflow vessel, as previously described, for allowing removal of at least a portion of the intermediate polar solvent solubilized resin phase. In certain embodiments, at least a majority of the polar solvent solubilized resin phase, and preferably substantially all of the polar solvent solubilized resin phase (i.e., at least 90% by volume) is removed in this manner. It should be understood that a relatively minor amount of polar solvent and solubilized resin may remain associated with the non-polar solvent viscous rubber phase. In certain embodiments of the second embodiment, the portion of the intermediate polar solvent solubilized resin phase (261) that is removed from the first intermediate fractionator (200) is transferred to a resin tank for storage or further processing and is not conveyed to any other fractionator. Accordingly, in certain embodiments of the processes disclosed herein, the polar solvent solubilized resin phase that is removed from the first fractionator and the first intermediate fractionator is not conveyed to any other fractionator.

The operation of any additional intermediate fractionators may proceed in a manner similar to the operation of the first fractionator (100) and the intermediate fractionator (200) as described above. The process according to the second embodiment as illustrated in FIG. 6 includes four intermediate fractionators (200, 300, 400, 500), which are connected in series with the first fractionator (100) and the final fractionator (600). The separation of the non-polar solvent viscous rubber phase from the polar solvent solubilized resin phase that occurs in the intermediate fractionators (300, 400, 500) proceeds as described with respect to intermediate fractionator (200). In addition, the non-polar solvent viscous rubber phase is allowed to flow out of the bottom outlet of the fractionator primary vessel and into the next successive fractionator. However, in certain embodiments of the second embodiment, such as the embodiment shown in FIG. 6, where the fractionation system comprises at least four intermediate fractionators, the polar solvent solubilized resin phase that is removed from at least three of the intermediate fractionators is fluidly conveyed to the preceding intermediate fractionator. For example, the polar solvent solubilized resin phase removed from intermediate fractionator (300) is fluidly conveyed via stream (361) to intermediate fractionator (200), the polar solvent solubilized resin phase removed from intermediate fractionator (400) is fluidly conveyed via stream (461) to intermediate fractionator (300), and the polar solvent solubilized resin phase removed from intermediate fractionator (500) is fluidly conveyed via stream (561) to intermediate fractionator (400).

As seen in FIG. 6, in certain embodiments, the polar solvent solubilized resin phase stream from an intermediate fractionator is combined with the non-polar solvent viscous rubber phase stream exiting the bottom outlet of the second preceding fractionator. For example, the polar solvent solubilized resin phase stream (361) from intermediate fractionator (300) is combined with the non-polar solvent viscous rubber phase stream (111) exiting the bottom outlet of the first fractionator (100) and is fed to intermediate fractionator (200), as seen in FIG. 6. In certain embodiments, where the polar solvent solubilized resin phase stream (361) from intermediate fractionator (300) is combined with the non-polar solvent viscous rubber phase stream (111), the combined stream flows through a static mixer (204) prior to entering intermediate fractionator (200). Similarly, in certain embodiments, the polar solvent solubilized resin phase stream (461) from intermediate fractionator (400) is combined with the non-polar solvent viscous rubber phase stream (211) exiting the bottom outlet of intermediate fractionator (200) and is fed to intermediate fractionator (300). In certain embodiments, where the polar solvent solubilized resin phase stream (461) from intermediate fractionator (400) is combined with the non-polar solvent viscous rubber phase stream (211), the combined stream flows through a static mixer (304) prior to entering intermediate fractionator (300). In certain embodiments, the polar solvent solubilized resin phase stream (561) from intermediate fractionator (500) is combined with the non-polar solvent viscous rubber phase stream (311) exiting the bottom outlet of intermediate fractionator (300) and is fed to intermediate fractionator (400). In certain embodiments, where the polar solvent solubilized resin phase stream (561) from intermediate fractionator (500) is combined with the non-polar solvent viscous rubber phase stream (311), the combined stream flows through a static mixer (404) prior to entering intermediate fractionator (400), as seen in FIG. 6. As previously mentioned, the polar solvent solubilized resin phase provides additional polar solvent to promote the separation of the non-polar solvent viscous rubber phase from the polar solvent solubilized resin phase in the fractionators.

With continued reference to FIG. 6, in certain embodiments, the intermediate non-polar solvent viscous rubber phase (411) of intermediate fractionator (400) is allowed to flow out of the bottom outlet of the intermediate fractionator primary vessel and into intermediate fractionator (500). As previously mentioned, additional polar solvent, and optionally additional non-polar solvent, may be added to the intermediate fractionator primary vessel to form a co-solvent based miscella mixture. Separation of the co-solvent based miscella mixture proceeds as previously described. In certain embodiments of the second embodiment, additional polar solvent and additional non-polar solvent (90) are added directly to the intermediate fractionator (500). In certain embodiments of the second embodiment, the additional polar solvent and additional non-polar solvent (90) is combined with the non-polar solvent viscous rubber phase (411) and the combined stream is fed into the intermediate fractionator (500). In certain embodiments, the additional non-polar solvent (90) flows through a heat exchanger (92) (supplied with appropriate plant utilities (U), e.g., hot water, cooling water, steam, etc.) to control the temperature of the non-polar solvent (90) being added to the process. In certain embodiments of the second embodiment, the polar solvent solubilized resin phase (661) that is removed from the final fractionator is fluidly conveyed to the preceding intermediate fractionator (500) to provide additional polar solvent to the intermediate fractionator (500). For example, in certain embodiments, as seen in FIG. 6, the polar solvent solubilized resin phase (661) removed from final fractionator (600) is combined with the non-polar solvent stream (90) and intermediate non-polar solvent viscous rubber phase stream (411) and the combined stream is fed into intermediate fractionator (500). In certain embodiments, where the polar solvent solubilized resin phase (661) from final fractionator (600) is combined with the non-polar solvent stream (90) and intermediate non-polar solvent viscous rubber phase (411), the combined stream flows through a static mixer (504) prior to entering intermediate fractionator (500), as seen in FIG. 6. In certain embodiments, the addition of polar solvent and non-polar solvent serves to promote separation of the non-polar solvent viscous rubber phase and the polar solvent solubilized resin phase.

As seen in FIG. 6, the intermediate non-polar solvent viscous rubber phase (511) is allowed to flow out of the bottom outlet of the intermediate fractionator primary vessel (i.e., the last intermediate fractionator (500)) and into the final fractionator (600). Additional polar solvent (80), and optionally additional non-polar solvent (90), is added to the final fractionator primary vessel to form a co-solvent based miscella mixture. In certain embodiments of the second embodiment, the additional polar solvent (80), and optionally additional non-polar solvent (90), is added directly to the final fractionator (600). In certain embodiments of the second embodiment, the additional polar solvent (80), and optionally additional non-polar solvent (90), is combined with the non-polar solvent viscous rubber phase (511) and the combined stream is fed into the final fractionator (600). In certain embodiments of the second embodiment, the additional polar solvent (80) is provided from a polar solvent storage tank and may flow through a heat exchanger (82) to control the temperature of the polar solvent (80) being added to the final fractionator (600). In certain embodiments of the second embodiment, the additional non-polar solvent (90) is provided from a non-polar solvent storage tank and may flow through a heat exchanger (92) to control the temperature of the non-polar solvent (90) being added to the final fractionator. In certain embodiments, where the additional polar solvent (80), the additional non-polar solvent (90), and the intermediate non-polar solvent viscous rubber phase (511) are combined, the combined stream flows through a static mixer (604) prior to entering the final fractionator (600), as seen in FIG. 6.

In certain embodiments of the second embodiment, the relative amount of polar solvent (80) added to the final fractionator (600) is greater than the amount of non-polar solvent added to the final fractionator (600). By adding relatively more polar solvent (80) than non-polar solvent (90), the concentration of solubilized rubber in the non-polar solvent viscous rubber phase (611) increases, which reduces the amount of non-polar solvent that will have to be removed from the non-polar solvent viscous rubber phase and also causes the rubber to drop out of solution.

Separation of the co-solvent based miscella mixture in the final fractionator (600) proceeds in the same manner as previously described with respect to the other fractionators. For example, after the co-solvent based miscella mixture is fed into the final fractionator (600), the mixture is allowed to separate into (i) a final non-polar solvent viscous rubber phase in a lower portion of the final fractionator primary vessel and (ii) a final polar solvent solubilized resin phase above the final non-polar solvent viscous rubber phase. During operation of the final fractionator a final vapor blanket is maintained above the final polar solvent solubilized resin phase in an upper portion of the final fractionator primary vessel.

During operation of the final fractionator (600) at least a portion of the final polar solvent solubilized resin phase is removed from the final fractionator primary vessel. For example, in certain embodiments of the second embodiment, the final fractionator may comprise an internal weir or an overflow vessel, as previously described, for allowing removal of at least a portion of the final polar solvent solubilized resin phase. In certain embodiments, at least a majority of the polar solvent solubilized resin phase, and preferably substantially all of the polar solvent solubilized resin phase (i.e., at least 90% by volume) is removed in this manner. It should be understood that a relatively minor amount of polar solvent and solubilized resin may remain associated with the non-polar solvent viscous rubber phase. As previously described, in certain embodiments of the second embodiment, the portion of the final polar solvent solubilized resin phase (661) that is removed from the final fractionator (600) is transferred to the preceding fractionator (500).

In accordance with the second embodiment, the final non-polar solvent viscous rubber phase (611) is allowed to flow out of the bottom outlet of the final fractionator primary vessel, thereby providing a separated solubilized rubber phase with reduced resin and polar solvent content as compared to the initial co-solvent based miscella. In certain embodiments, the final non-polar solvent viscous rubber phase (611) is transferred to a storage tank where it can undergo additional processing to provide a purified rubber product.

The process according to the second embodiment as described herein is preferably conducted on a continuous basis. For example, a continuous stream of initial co-solvent based miscella (50) may be fed into the fractionation system (1000) and a continuous stream of final non-polar solvent viscous rubber phase (611) may exit the fractionation system (1000).

Solvents

In any of the embodiments of the processes disclosed herein, the solvents contained within the co-solvent based miscella and any additional solvents (polar solvent, non-polar solvent, or a combination thereof) added elsewhere to the process may be the same or different (i.e., overall one non-polar solvent may be utilized and overall one polar solvent may be utilized, or alternatively more than one of each maybe be utilized.). Preferably, all non-polar solvent utilized within the process are the same and all polar solvent utilized within the process are the same.

In any of the foregoing embodiments of the processes disclosed herein, the at least one polar solvent of the co-solvent based miscella and any additional polar solvent added elsewhere to the process may be selected from the group consisting of alcohols having 1 to 8 carbon atoms (e.g., ethanol, isopropanol, ethanol and the like); ethers and esters having from 2 to 8 carbon atoms; cyclic ethers having from 4 to 8 carbon atoms; and ketones having from 3 to 8 carbon atoms (e.g., acetone, methyl ethyl ketone and the like); and combinations thereof. In certain preferred embodiments of the processes disclosed herein, the at least one non-polar solvent of the co-solvent based miscella and any additional non-polar solvent added elsewhere in the process are each hexane or cyclohexane, and the at least one polar solvent of the co-solvent based miscella and any additional polar solvent added elsewhere in the process is optionally acetone. Other polar solvents (individually or in combination) may be used in embodiments of the processes disclosed herein as long as the polar solvent preferentially solvates a portion of non-rubber extractables (e.g., resins) and acts (at a certain concentration) to coagulate natural rubber. In any of the embodiments of the processes disclosed herein, mixtures of two or more polar solvents may be utilized.

In any of the foregoing embodiments of the processes described herein, the at least one non-polar solvent that is contained in the co-solvent based miscella and any additional non-polar solvent added elsewhere in the process may be selected from the group consisting of alkanes having from 4 to 9 carbon atoms (e.g., pentane, hexane, heptanes, nonane and the like); cycloalkanes and alkyl cycloalkanes having from 5 to 10 carbon atoms (e.g., cyclohexane, cyclopentane and the like); aromatics and alkyl substituted aromatics having from 6 to 12 carbon atoms (e.g., benzene, toluene, xylene and the like); and combinations thereof. In certain preferred embodiments according of the processes disclosed herein, the at least one polar solvent of the co-solvent based miscella and any additional polar solvent added to the process is acetone, and the at least one non-polar solvent of the co-solvent based miscella and any additional non-polar solvent added to the process are optionally hexane or cyclohexane. Other non-polar solvents (individually or in combination) may be used in embodiments of the processes disclosed herein as long as the non-polar solvent preferentially solvates natural rubber. In any of the embodiments of the processes disclosed herein, mixtures of two or more non-polar solvents may be utilized.

To the extent that the term "includes" or "including" is used in the specification or the claims, it is intended to be inclusive in a manner similar to the term "comprising" as that term is interpreted when employed as a transitional word in a claim. Furthermore, to the extent that the term "or" is employed (e.g., A or B) it is intended to mean "A or B or both." When the applicants intend to indicate "only A or B but not both" then the term "only A or B but not both" will be employed. Thus, use of the term "or" herein is the inclusive, and not the exclusive use. See Bryan A. Garner, *A Dictionary of Modern Legal Usage* 624 (2d. Ed. 1995). Also, to the extent that the terms "in" or "into" are used in the specification or the claims, it is intended to additionally mean "on" or "onto." Furthermore, to the extent the term "connect" is used in the specification or claims, it is intended to mean not only "directly connected to," but also "indirectly connected to" such as connected through another component or components.

While the present application has been illustrated by the description of embodiments thereof, and while the embodiments have been described in considerable detail, it is not the intention of the applicants to restrict or in any way limit the scope of the appended claims to such detail. Additional advantages and modifications will readily appear to those skilled in the art. Therefore, the application, in its broader aspects, is not limited to the specific details, the representative apparatus, and illustrative examples shown and described. Accordingly, departures may be made from such details without departing from the spirit or scope of the applicant's general inventive concept.

What is claimed is:

1. A fractionator for separating solubilized rubber from a co-solvent based miscella, the fractionator comprising:
    a primary vessel comprising:
        a feed inlet for feeding a co-solvent based miscella into the primary vessel, wherein the co-solvent based miscella separates to form (i) a non-polar solvent viscous rubber phase in a lower portion of the primary vessel and (ii) a polar solvent solubilized resin phase above the non-polar solvent viscous rubber phase;
        a side outlet for removing the polar solvent solubilized resin phase from the primary vessel; and
        a bottom outlet for removing the non-polar solvent viscous rubber phase from the primary vessel.

2. The fractionator of claim 1, further comprising an overflow vessel having an inlet and an outlet, wherein the overflow vessel inlet is fluidly connected to the side outlet such that the polar solvent solubilized resin phase flows through the side outlet into the overflow vessel and is removed through the overflow vessel outlet.

3. The fractionator of claim 1, wherein the primary vessel further comprises an internal weir, wherein the side outlet is bounded by the internal weir such that the polar solvent solubilized resin phase flows over the internal weir to remove the polar solvent solubilized resin phase through the side outlet.

4. The fractionator of claim 3, wherein the internal weir forms a wall around at least a portion of the circumference of an upper interior portion of the primary vessel.

5. The fractionator of claim 1, wherein the primary vessel further comprises at least one of:
    a gas inlet for adding a vapor blanket to the fractionator, or
    a gas outlet for purging vapor from the fractionator.

6. The fractionator of claim 1, wherein the primary vessel further comprises at least one solvent inlet for feeding solvent to the primary vessel.

7. The fractionator of claim 1, further comprising at least one additional fractionator connected in series, wherein each additional fractionator has a feed inlet that is fluidly connected to the bottom outlet of the preceding fractionator.

8. The fractionator of claim 7, wherein each additional fractionator further comprises a polar solvent inlet for addition of polar solvent.

9. The fractionator of claim 7, comprising a total of six fractionators connected in series, wherein at least one of the intermediate fractionators further comprises a resin phase feed line that is fluidly connected to the preceding fractionator.

10. A fractionator for separating solubilized rubber from a co-solvent based miscella, the fractionator comprising:
    a primary vessel comprising:
        a feed inlet for feeding a co-solvent based miscella into the primary vessel, wherein the co-solvent based miscella separates to form (i) a non-polar solvent viscous rubber phase in a lower portion of the primary vessel and (ii) a polar solvent solubilized resin phase above the non-polar solvent viscous rubber phase;
a side outlet for removing the polar solvent solubilized resin phase from the primary vessel; and
a bottom outlet for removing the non-polar solvent viscous rubber phase from the primary vessel;
an overflow vessel having an inlet and an outlet, wherein the overflow vessel inlet is fluidly connected to the side outlet such that the polar solvent solubilized resin phase flows through the side outlet into the overflow vessel and is removed through the overflow vessel outlet; and
at least one additional fractionator connected in series, wherein each additional fractionator has a feed inlet that is fluidly connected to the bottom of the preceding fractionator, and
wherein the primary vessel further comprises an internal weir, wherein the side outlet is bounded by the internal weir such that the polar solvent solubilized resin phase flows over the internal weir to remove the polar solvent solubilized resin phase through the side outlet.

11. A process for separating solubilized non-*Hevea* rubber from a co-solvent based miscella, the process comprising:
(a) providing an initial co-solvent based miscella comprising at least one polar solvent, at least one non-polar solvent, solubilized non-*Hevea* rubber, and solubilized resin;
(b) using a fractionation system comprising multiple fractionators in series to separate the initial co-solvent based miscella into at least two phases, wherein the multiple fractionators include a first fractionator, one or more intermediate fractionators, and a final fractionator, and wherein each fractionator comprises a primary vessel having (i) a feed inlet, (ii) a side outlet, (iii) a bottom outlet, and (iv) an internal weir between the interior of the primary vessel and the side outlet or an overflow vessel external to the primary vessel and fluidly connected to the side outlet;
wherein the initial co-solvent based miscella is fed into the first fractionator primary vessel through the first fractionator primary vessel feed inlet, and the initial co-solvent based miscella separates to form (i) a first non-polar solvent viscous rubber phase in a lower portion of the first fractionator primary vessel and (ii) a first polar solvent solubilized resin phase above the first non-polar solvent viscous rubber phase, and wherein a first vapor blanket is maintained above the first polar solvent solubilized resin phase in an upper portion of the first fractionator primary vessel;
(c) allowing at least a portion of the first polar solvent solubilized resin phase to flow over the internal weir of the first fractionator or into the overflow vessel of the first fractionator for removal from the first fractionator primary vessel through the side outlet;
(d) allowing the first non-polar solvent viscous rubber phase to flow out of the bottom outlet of the first fractionator primary vessel and into an intermediate fractionator;
(e) adding additional polar solvent and optionally additional non-polar solvent to the intermediate fractionator primary vessel to form a co-solvent based miscella mixture with the non-polar solvent viscous rubber phase from the first fractionator primary vessel and allowing for separation of that mixture into (i) an intermediate non-polar solvent viscous rubber phase in a lower portion of the intermediate fractionator primary vessel and (ii) an intermediate polar solvent solubilized resin phase above the intermediate non-polar solvent viscous rubber phase, and wherein an intermediate vapor blanket is maintained above the intermediate polar solvent solubilized resin phase in an upper portion of the intermediate fractionator primary vessel;
(f) allowing at least a portion of the intermediate polar solvent solubilized resin phase to flow over the internal weir of the intermediate fractionator or into the overflow vessel of the intermediate fractionator for removal from the intermediate fractionator primary vessel through the side outlet;
(g) allowing the intermediate non-polar solvent viscous rubber phase to flow out of the bottom outlet of the intermediate fractionator primary vessel and into the final fractionator;
(h) adding additional polar solvent and optionally additional non-polar solvent to the final fractionator primary vessel to form a co-solvent based miscella mixture with the non-polar solvent viscous rubber phase from the intermediate fractionator primary vessel and allowing for separation of that mixture into (i) a final non-polar solvent viscous rubber phase in a lower portion of the final fractionator primary vessel and (ii) a final polar solvent solubilized resin phase above the final non-polar solvent viscous rubber phase, and wherein a final vapor blanket is maintained above the final polar solvent solubilized resin phase in an upper portion of the final fractionator primary vessel;
(i) allowing at least a portion of the final polar solvent solubilized resin phase to flow over the internal weir of the final fractionator or into the overflow vessel of the final fractionator for removal from the final fractionator primary vessel; and
(j) allowing the final non-polar solvent viscous rubber phase to flow out of the bottom outlet of the final fractionator primary vessel, thereby providing a separated solubilized rubber phase with reduced resin and polar solvent content as compared to the initial co-solvent based miscella.

12. The process of claim 11, wherein polar solvent is added to the initial co-solvent based miscella prior to or after the initial co-solvent based miscella is fed into the first fractionator primary vessel.

13. The process of claim 11, wherein at least two intermediate fractionators are used and each additional intermediate fractionator is connected in series and positioned between the first fractionator and the final fractionator.

14. The process of claim 11, wherein the primary vessel of each fractionator comprises an internal weir and the side outlet of each fractionator is bounded by the internal weir such that the polar solvent resin phase flows over the internal weir to remove the polar solvent resin phase through the side outlet, and wherein the internal weir forms a wall around at least a portion of the circumference of an upper interior portion of the primary vessel.

15. The process of claim 11, wherein each fractionator comprises an overflow vessel external to the primary vessel, wherein the overflow vessel comprises an inlet and an outlet, wherein the overflow inlet is fluidly connected to the side outlet such that the polar solvent resin phase flows through the side outlet into the overflow vessel and is removed through the overflow vessel outlet.

16. The process of claim 11, wherein the fractionation system comprises at least four intermediate fractionators, wherein the polar solvent solubilized resin phase that is removed from at least three of the intermediate fractionators is fluidly conveyed to the preceding intermediate fractionator.

17. The process of claim 11, wherein the polar solvent solubilized resin phase that is removed from the final fractionator is fluidly conveyed to the preceding intermediate fractionator.

18. The process of claim 11, wherein the polar solvent solubilized resin phase that is removed from the first fractionator and the first intermediate fractionator is not conveyed to any other fractionator.

19. The process of claim 11, wherein the non-*Hevea* rubber is from guayule.

20. The process of claim 11, wherein at least one of the following is met:
   the at least one polar solvent comprises acetone; or
   the at least one non-polar solvent comprises hexane.

* * * * *